United States Patent [19]

Kikuchi

[11] Patent Number: 5,007,407
[45] Date of Patent: Apr. 16, 1991

[54] ENDOSCOPE HAVING PICTURE IMAGE FREEZE DEVICE

[75] Inventor: Katsuya Kikuchi, Tochigi, Japan

[73] Assignee: Kabushiki Kaisha Toshiba, Kawasaki, Japan

[21] Appl. No.: 397,784

[22] Filed: Aug. 23, 1989

[30] Foreign Application Priority Data

Aug. 23, 1988 [JP]  Japan .................... 63-207436

[51] Int. Cl.$^5$ .................... A61B 1/04; A61B 1/06
[52] U.S. Cl. .................................... 128/6; 358/98
[58] Field of Search .................... 273/4, 6; 358/98

[56] References Cited

U.S. PATENT DOCUMENTS 4,740,837  4/1988  Yanagisawa et al. ............ 358/98

Primary Examiner—William H. Grieb
Attorney, Agent, or Firm—Foley & Lardner

[57] ABSTRACT

An endoscope including a scope, in which a light source emits at least one light pulse locating in a boundary portion of adjacent first and second fields, and a photoelectric device detects image signals from the light pulse, and wherein a processor determines a difference between first and second field illuminances of the light pulse from the image signals, and a controller controls, depending on the difference, to reduce the difference to at least a certain value to obtain a frozen picture image having a high resolving power without causing a flicker therein.

15 Claims, 8 Drawing Sheets

ENDOSCOPE HAVING PICTURE IMAGE FREEZE DEVICE

BACKGROUND OF THE INVENTION

1. Field of the Invention

The present invention relates to an endoscope including a picture image freeze device, and more particularly to improvement in the quality of a frozen picture image in an endoscope.

2. Description of the Background Art

In a conventional endoscope, a frame of picture image composed of odd and even fields is simultaneously obtained by using a color camera device such as a CCD during the operation of the endoscope.

When a frozen picture image is reproduced by the frame of picture, usually, a light pulse or pulsed light is irradiated to an object to be observed, extending over the boundary between the adjacent two fields, i.e. odd and even fields in order to reduce the discord or disagreement of the reproduced picture images due to the time difference between the two fields, as schematically shown in FIG. 1, wherein a VD signal represents a TV vertical synchronization drive signal.

However, when an object is moved during the operation, and a light pulse having a long pulse width is used, there happens the discord or disagreement between the picture images of the odd and even fields. Hence, when the picture image is reproduced in such a discord or disagreement situation, a flicker is caused in the reproduced picture image, which is troublesome and hard to observe the picture image.

In turn, when the pulse width of the light pulse is small, the flicker to be caused by the moving of the object is prevented, but a slight shift of timing for emitting the light pulse or a deformation of a wave form of the light pulse can readily vary the ratio of illuminance between the odd and even fields to cause a flicker.

In another conventional endoscope, a frozen picture image is reproduced by using the picture image of one of the odd and even fields. However, in such a case, although the flicker can be effectively prevented, the inherent resolving power provided in an endoscope of this kind is reduced by half.

SUMMARY OF THE INVENTION

It is therefore an object of the present invention to provide an endoscope, free from the aforementioned disadvantages and defects of the prior art, which is capable of effectively preventing a flicker and reproducing a picture image having a high resolving power.

In accordance with one aspect of the present invention, there is provided an endoscope including a scope, comprising light source means for emitting at least one light pulse locating in a boundary portion of adjacent first and second fields, means for obtaining photo-electrically a detection signal from the light pulse, means for operating a difference between first and second field illuminances of the light pulse from the detection signal, and means for controlling the light source means depending on the difference to reduce the difference to at least a certain value.

In accordance with another aspect of the present invention, there is provided an endoscope including a scope, comprising light source means for emitting a light pulse extending over a boundary between adjacent first and second fields, means for obtaining photoelectrically a detection signal from the light pulse, means for operating a difference between first and second field illuminances of the light pulse from the detection signal, and means for controlling the light source means depending on the difference to reduce the difference to at least a certain value.

In accordance with still another aspect of the present invention, there is provided an endoscope including a scope, comprising light source means for emitting at least one light pulse locating in a boundary portion of adjacent first and second fields, means for obtaining photo-electrically a detection signal from the light pulse, means for operating a difference between first and second field illuminances of the light pulse from the detection signal, and means for electrically controlling one of the detected first and second field illuminances to reduce the difference to at least a certain value.

BRIEF DESCRIPTION OF THE DRAWINGS

The above and other objects, features and advantages of the present invention will be more apparent from the following description of the preferred embodiments with reference to the accompanying drawings, in which.

DESCRIPTION OF THE PREFERRED EMBODIMENTS

Figure 1:
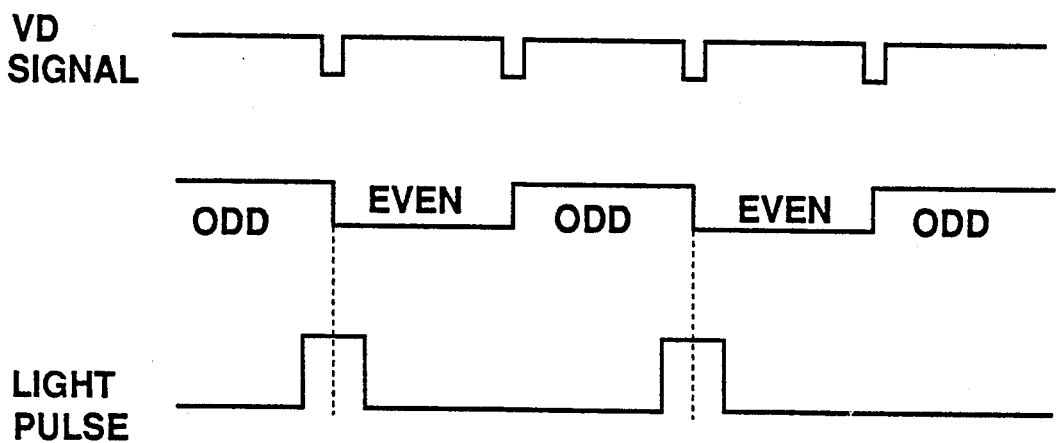
FIG. 1 is a timing chart schematically showing a conventional process for obtaining a frame of picture image.
Figure 2:
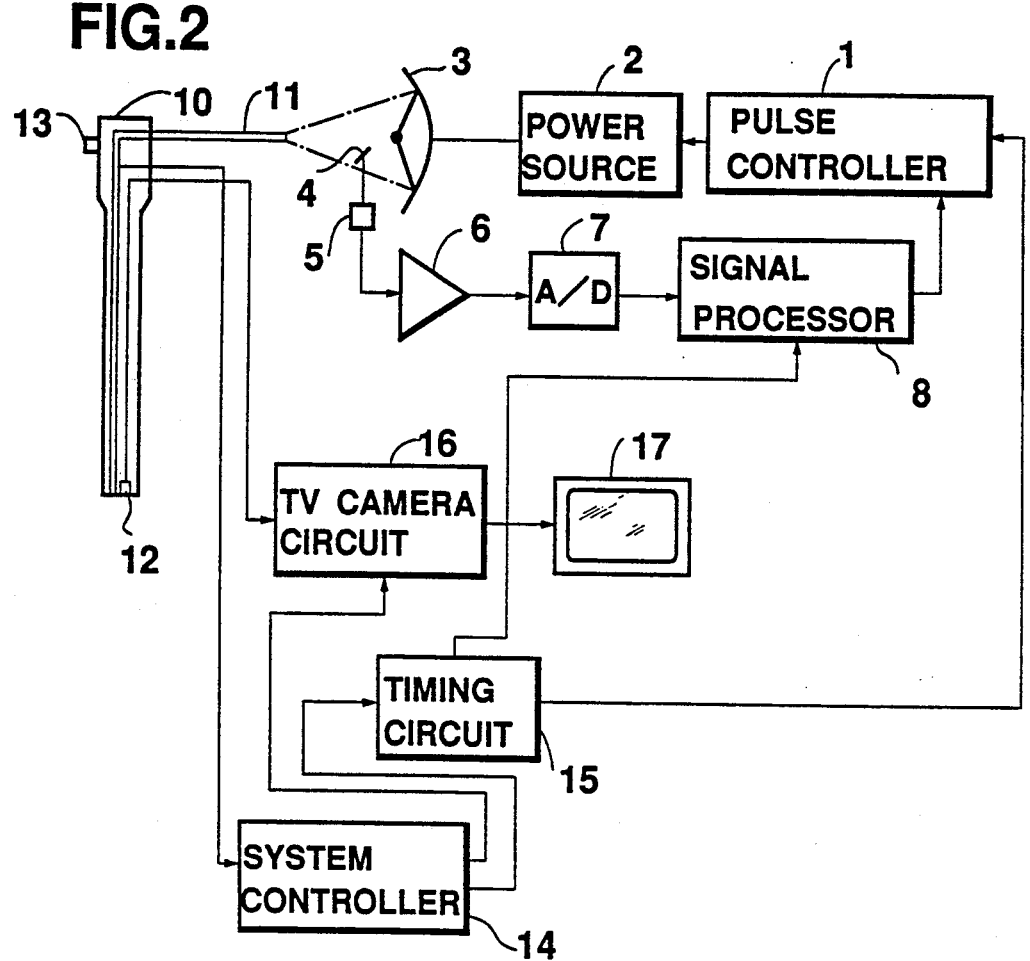
FIG. 2 is a block diagram of a first embodiment of an endoscope according to the present invention.

Referring now to the drawings, wherein like reference characters designate like or corresponding members throughout the several views, there is shown in FIG. 2 a first embodiment of an endoscope according to the present invention.

In the drawing, according to the control of a pulse controller 1, a light source 3 for illumination is allowed to emit pulsed light or a light pulse by driving a power source 2, and the emitted light pulse is partially reflected to a photoelectric device 5 such as a photodiode by a half mirror 4. The photoelectric device 5 outputs a signal having an intensity corresponding to the illuminance of the light source 3 to an analog-digital (A/D) converter 7 via an amplifier 6, and the A/D converter 7 sends digital signals to a signal processor 8.

The endoscope is provided with a scope 10 including a light guide 11, a solid-state image pickup device 12, such as a CCD, for photographing an object to be observed, and a freeze switch 13. The light pulse emitted by the light source 3 is converged on the inlet end of the light guide 11 of the scope 10 so as to illuminate the object from the end of the scope 10.

A system controller 14 controls the entire system of the endoscope, and outputs a signal to a timing circuit 15 and a TV camera circuit 16, as hereinafter described in detail. The timing circuit 15 sends a light pulse control signal to the pulse controller 1, and the pulse controller 1 controls to drive the power source 2, as hereinafter described in detail. The image pickup device 12 outputs image signals to the TV camera circuit 16 which converts the image signals to color video signals and sends the color video signals to a display 17. The display 17 displays a picture image of the object thereon.

Figure 3:
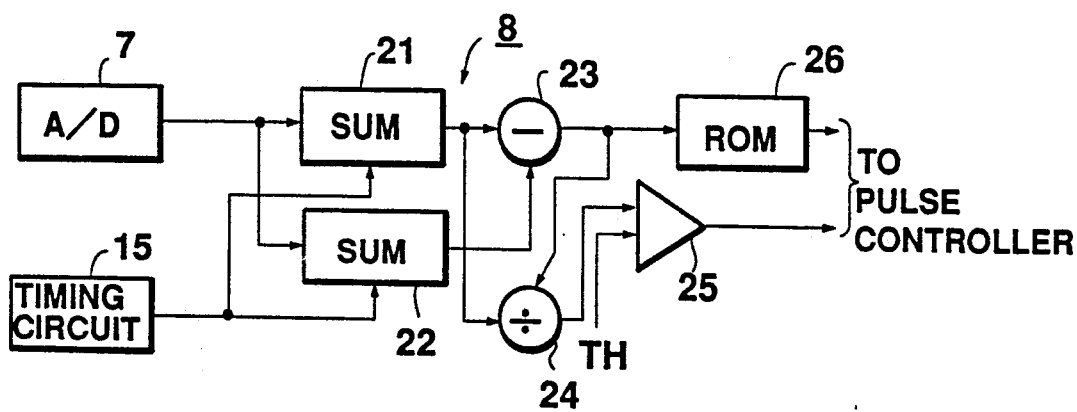
FIG. 3 is a block diagram of a signal processor shown in FIG. 2.

There is shown in FIG. 3 one embodiment of the signal processor 8 shown in FIG. 2, which comprises a pair of summing (sum) circuits 21 and 22, a subtracter circuit 23, a divider circuit 24, a comparator circuit 25 and a ROM circuit 26, as hereinafter described in detail. When the freeze switch 13 of the scope 10 is switched on by an operator, the system controller 14 outputs a freeze signal to the timing circuit 15 to start a freeze process. The A/D 7 sends the digital signals to the sum circuits 21 and 22, and the timing circuit 15 outputs a TV vertical synchronization drive signal or a VD signal to the sum circuits 21 and 22.

The sum circuit 21 is actuated in the odd field periods in synchronization with the VD signal to output a digital signal representing an odd field illuminance to the subtracter circuit 23 and divider circuit 24, and the sum circuit 22 is actuated in the even field periods in synchronization with the VD signal to output a digital signal representing an even field illuminance to the subtracter circuit 23. The subtracter circuit 23 operates a difference between the odd and even field illuminances and outputs a digital signal representing the resulted illuminance difference to the divider circuit 24 and the ROM circuit 26. The divider circuit 24 operates to divide the output signal of the subtracter circuit 23 by the output signal of the sum circuit 21 to output a digital signal representing the operated result to the comparator circuit 25.

The comparator circuit 25 compares the output signal of the divider circuit 24 with a predetermined threshold value to obtain a comparison result. When the output signal of the divider circuit 24 is at most the threshold value, the comparator circuit 25 sends a first control signal to the pulse controller 1 so that the first control signal allows to radiate the light pulse at the predetermined timing, i.e., not to change the radiation timing of the light pulse. In turn, when the output signal of the divider circuit 24 is more than the threshold value, the comparator circuit 25 sends a second control signal to the pulse controller 1 so that the second control signal allows to change or correct the radiation timing of the light pulse depending on the difference between the odd and even field illuminances.

The ROM circuit 26 stores the delay time DT of the radiation timing of the light pulse only when the difference between the odd and even field illuminances is more than the threshold value, and outputs the light pulse control signal along with the delay time DT to the pulse controller 1 in response to such an illuminance difference fed from the subtracter circuit 23. The pulse controller 1 is operated and controlled by the output signals of the comparator 25 and ROM circuit 26 in synchronization with the VD signal fed from the timing circuit 15 to drive and control the power source 2.

In FIGS. 4a, 4b, 4c and 5d, there are shown a VD signal, a freeze signal, a light pulse control signal with delay time DT, and a light pulse having time length $\Delta T$ such as 1 to 2 milliseconds with illuminances of odd and even fields, extending over a boundary therebetween, respectively.

The system controller 14 outputs the VD signal shown in FIG. 4a to the TV camera circuit 16. When the freeze switch 13 is switched on, the freeze-on instruction is fed to the system controller 14, and the system controller 14 sends the freeze signal shown in FIG. 4b to the timing circuit 15. The timing circuit 15 outputs the light pulse control signal shown in FIG. 4c to the pulse controller 1 during the freeze period, the light pulse control signal rising at its leading edge soon after the predetermined delay time DT from the timing of the trailing edge of the VD signal in the even field. Accordingly, the power source 2 is controlled to be driven by the pulse controller 1 in synchronization with the light pulse control signal, and thus the light source 3 radiates the light pulse extending over the boundary between the odd and even fields, as shown in FIG. 4d.

When the difference $\Delta$ between the odd and even field illuminances A and B of the light pulse emitted by the light source 3 is large, flicker is caused in the frozen picture image, and it becomes unclear and hard to observe it.

Figure 5:
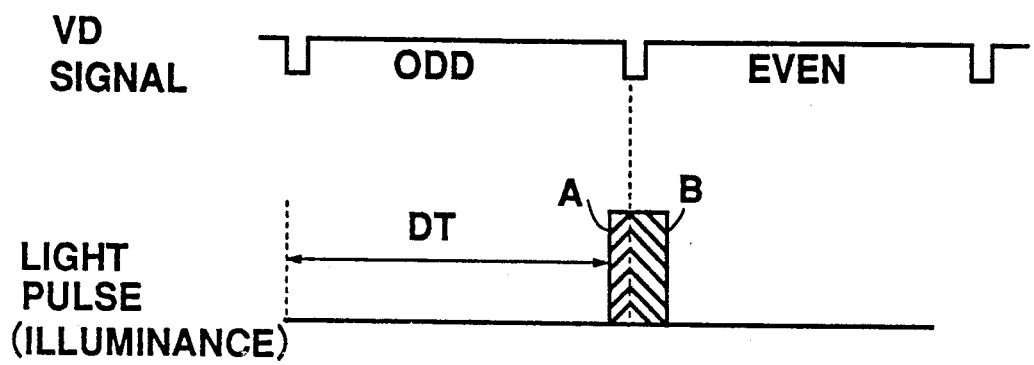
FIG. 5 is a timing chart, FIG. 4, schematically showing an example of illuminance of odd and even fields with a illuminance difference from one another therebetween in the endoscope shown in FIG. 2

Then, the difference $\Delta = (A - B)$ between the odd and even field illuminances A and B is obtained by a combination of the sum circuits 21 and 22 and subtracter circuit 23 of the signal processor 8 shown in FIG. 3. For example, as shown in FIG. 5, when an odd field illuminance A is smaller than an even field illuminance B in a light pulse, the difference $\Delta$ between the odd and even field illuminances A and B is negative, and hence the delay time DT shown in FIG. 5 is reduced. In turn, when the difference between the odd and even field illuminances of the light pulse is positive, the delay time DT is increased.

However, it has been confirmed from experiments that, when the output $(A - B)/A$ or $\Delta/A$ of the divider circuit 24 of the signal processor 8, as shown in FIG. 3, is approximately 0.03, the flicker caused in the frozen picture image could be ignored.

Figure 6:
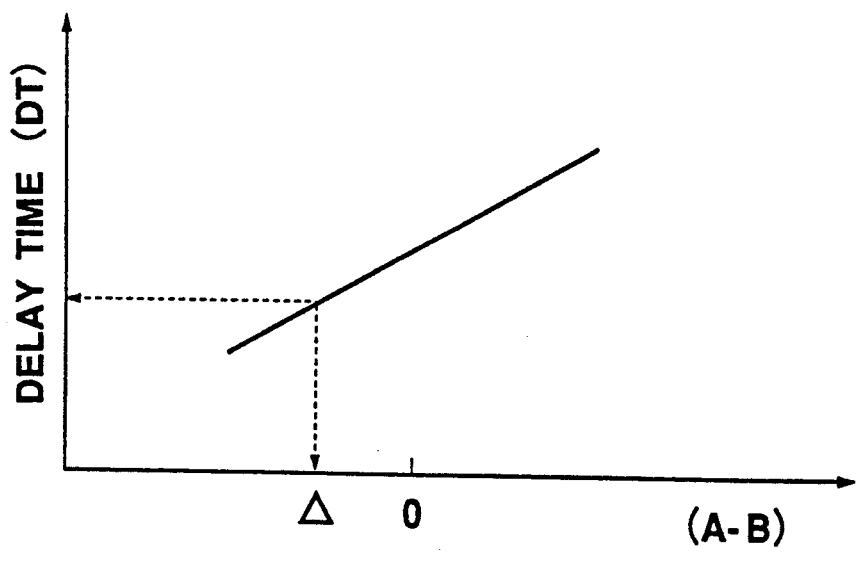
FIG. 6 is a graphical representation of a characteristics line of a delay time for defining a light pulse emitting timing with reference to an illuminance difference between odd and even fields according to the present invention.

Hence, in this embodiment, for instance, the value to be stored in the ROM circuit 26 of the signal processor 8 is determined to $\Delta/A = 0.03$ as a threshold value according to a characteristics line (which can be considered to be linear characteristics) of the illuminance difference $(A - B)$ with respect to the delay time DT, as shown in FIG. 6. Thus, the comparator 25 discriminates whether the output of the divider circuit 24 is within $\Delta/A = 0.03$ or not.

When the output of the divider circuit 24 is within $\Delta/A = 0.03$, no control for changing the illuminance difference Δ is carried out, and hence the power source 2 is controlled to be driven using the delay time DT stored in the ROM circuit 26 by the pulse controller 1. In the initial freeze process, the delay time DT stored in the ROM circuit 26 is set as it is in the pulse controller 1.

When the output of the divider circuit 24 is more than Δ/A=0.03, the delay time DT is changed to a new value in the pulse controller 1 regardless of the positive or negative value of Δ/A, and the power source 2 is controlled and is driven using the new delay time by the pulse controller 1.

In this embodiment, as described above, when the ratio between the odd and even field illuminances of the light pulse is unbalanced in the freeze process, the difference between the odd and even field illuminances A and B of the light pulse is operated in the signal processor 8 on the basis of the detection of the light pulse in the photoelectric device 5, and the delay time DT of the light pulse is so changed in the pulse controller 1 that the difference between the odd and even field illuminances of the light pulse may be within a certain range of values, or the output (A−B)/A of the divider circuit of the signal processor may be within a certain threshold value. As a result, a frozen picture image with high resolving power can be obtained without causing the flicker.

In practice, as the illumination period of the lamp of the light source 3 is extended, the wave form of the light pulse is changed, but its change is quite slow. Hence, in view of this fact, when the delay time DT of the light pulse for controlling the radiation timing of the light pulse is once determined, no serious problem takes place even after the lamp of the light source is used for a long period of time without changing the delay time DT of the light pulse.

Figure 7:
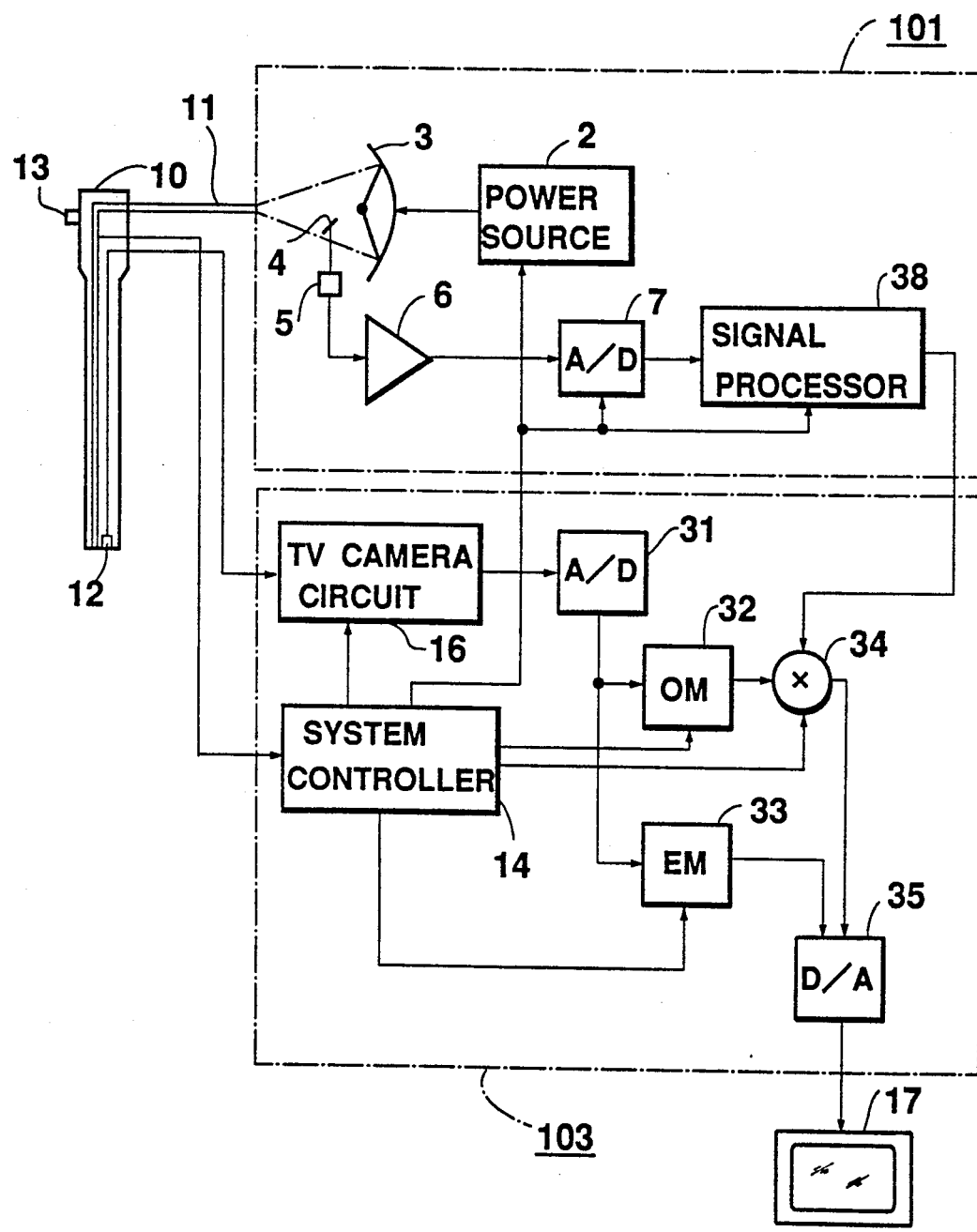
FIG. 7 is a block diagram of a second embodiment of an endoscope according to the present invention.

In FIG. 7, there is shown a second embodiment of an endoscope according to the present invention, having a similar construction to the first embodiment shown in FIG. 2.

In this embodiment, as shown in FIG. 7, the endoscope comprises a scope 10, a light source section 101 and a processing body section 103. The light source section 101 includes a power source 2, a light source 3, a photoelectric device 5, an amplifier 6, an A/D converter 7 and a signal processor 38 for operating a ratio between odd and even field illuminances of an object to be observed, and the processing body section 103 includes a system controller 14, a TV camera circuit 16, an A/D converter 31, OM and EM memories 32 and 33 for storing odd and even field picture images, respectively, a multiplier 34, a digital-analog (D/A) converter 35 and a display 17, as hereinafter described in detail.

The TV camera circuit 16 receives image signals from the image pickup device 12 of the scope 10, converts the image signals to color video signals, and sends the color video signals to the A/D converter 31. The A/D converter 31 converts the color video signals to digital color video signals, and outputs the digital color video signals to the OM and EM memories 32 and 33 for storing these signals.

The multiplier 34 multiplies the output of the OM memory 32 by a correction value on the basis of the output signal of the signal processor 38, and sends the corrected color video signals to the display 17 through the D/A converter 35. The EM memory 33 outputs the color video signals to the display 17 through the D/A converter 35. The display 17 displays a picture image according to the analog color video signals fed from the D/A converter 35.

Figure 8:
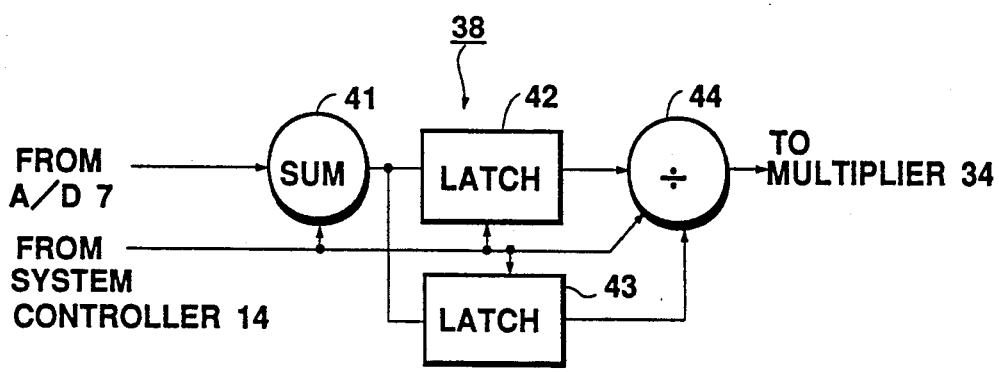
FIG. 8 is a block diagram of a signal processor shown in FIG. 7.

In FIG. 8, there is shown one embodiment of the signal processor 38 for operating a ratio between odd and even field illuminances $S_O$ and $S_E$ of a light pulse, which comprises a summing circuit (SUM) 41, a pair of latch circuits (LATCHs) 42 and 43 for odd and even field illuminances, and a divider circuit 44, as hereinafter described in detail.

Figure 4:
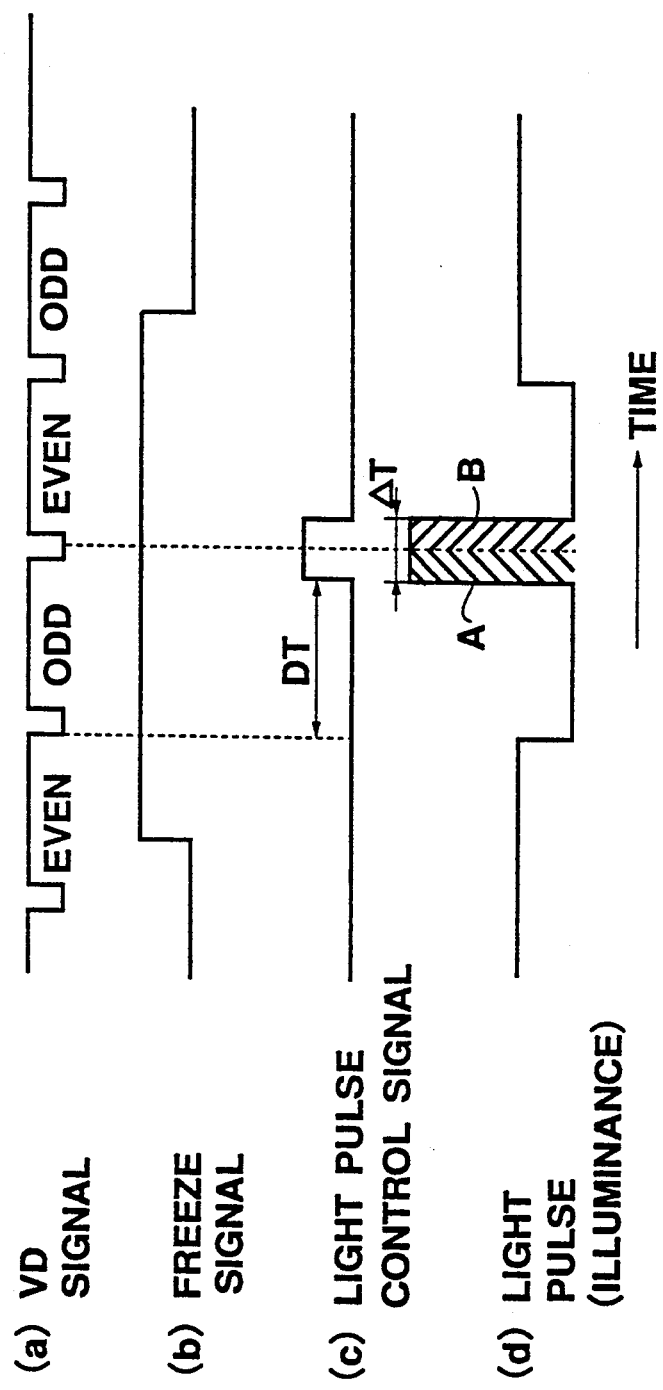
FIG. 4 is a timing chart schematically showing signals and illuminance in an operation for obtaining a frame of picture image in the endoscope shown in FIG. 2.
Figure 9:
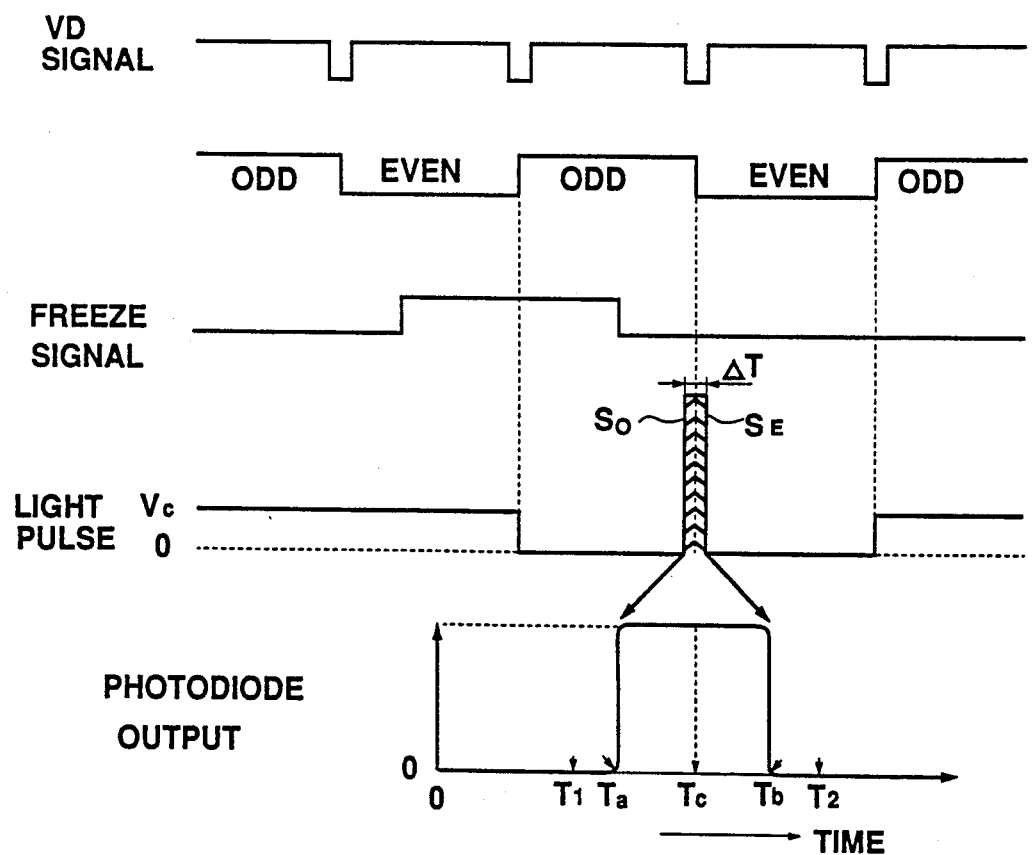
FIG. 9 is a timing chart schematically showing an operation for obtaining a frame of picture image in the endoscope shown in FIG. 7.

FIG. 9 shows, like FIG. 4, the VD signal, a freeze signal and a light pulse having time length ΔT such as 1 to 2 milliseconds, for operating a freeze process.

Now, when the freeze switch 13 is switched on, as shown in FIG. 9, the freeze signal is output, and the light source 3 is moved into a pulse radiation mode from the beginning of one odd field section soon after the leading timing of the freeze signal. That is, from the beginning of this odd field section, the illuminance goes from the on state to the off state, and then a strong light pulse is emitted from the light source 3 for a quite short period ΔT between the end portion of this odd field section and a beginning portion of a next even field section adjacent thereto, i.e., extending over the boundary between the adjacent odd and even field sections. Thereafter, the illuminance becomes off to the end of this even field section, and then the illumination continuously becomes on again. On this occasion, the odd field picture image data is stored in the OM memory 32, and the even field picture image data is stored in the EM memory 33. The time difference between the odd and even field picture images is determined by the short period ΔT. Since the time difference is quite small, the problem such as the discord or disagreement of the reproduced picture images of the object in the odd and even fields can be ignored, and thus the flicker can be effectively prevented.

However, the difference between the odd and even field illuminances $S_O$ and $S_E$ for use in reproducing the odd and even field picture images may be caused by the deformation of the wave form of the light pulse or the jitter of the synchronization of the light pulse radiation timing to cause the flicker when the frozen picture image is reproduced.

In this embodiment, in order to measure the illuminances $S_O$ and $S_E$ of the light pulse, the sampling in the A/D converter 7 is started at the beginning of the odd field section and is carried out in a period between times $T_1$ and $T_2$, as shown in the lowermost portion of FIG. 9. $T_1$ is set before a leading time Ta of the light pulse, and $T_2$ is set after a trailing time Tb of the light pulse. Tc is a time of transference from the odd field section to the even field section.

The ratio between the odd and even field illuminances $S_O$ and $S_E$ is operated by the signal processor 38. The output signals of the photoelectric device 5 are amplified in the amplifier 6 and are digitalized in the A/D converter 7. The digitalized output signals of the A/D converter 7 are summed in the period between $T_1$ and Tc in the SUM 41, and the summed result is stored in the LATCH 42. Then, the digitalized output signals of the A/D converter 7 are summed in the period between Tc and $T_2$ in the SUM 41, and the summed result is stored in the LATCH 43. The summed results of the LATCHs 42 and 43 are sent to the divider circuit 44 in which the ratio of the summed results is calculated.

For instance, when the odd field illuminance is 1.1 times larger than that of the even field illuminance, the divider circuit 44 outputs a value 1.1 to the multiplier 34. In the multiplier 34, a reciprocal number, e.g., 1/1.1 in this case, of the output of the divider circuit 44 is multiplied as a correction value to the odd field picture image data fed from the OM memory 32 in order to correct the difference between the odd and even field illuminances or to correct the discord or disagreement of the odd and even picture images. The corrected odd field picture image data and the even field picture image data is fed from the multiplier 34 and the EM memory 33 to the D/A converter 35 in which the picture image data is converted into the analog picture image signals. The analog picture image signals are sent to the display for displaying the frozen picture image thereon. During displaying the frozen picture image on the display, the input of the picture image date into the OM and EM memories 32 and 33 is forbidden, and the stored picture image data is repeatedly read out of the memories 32 and 33 for display the picture image. In this case, the operation relating to the freeze process is controlled by the system controller 14.

As described above, in this embodiment, when a light pulse of an extremely short time length is irradiated to an object to be observed in order to obtain one frame of frozen picture image, the discord or disagreement between the odd and even field signal intensity can be effectively corrected to prevent the flicker in the reproduced picture image and thus to obtain a frozen picture image having a high resolving power. In this embodiment, the same effects and advantages as those of the first embodiment can be obtained.

Figure 10:
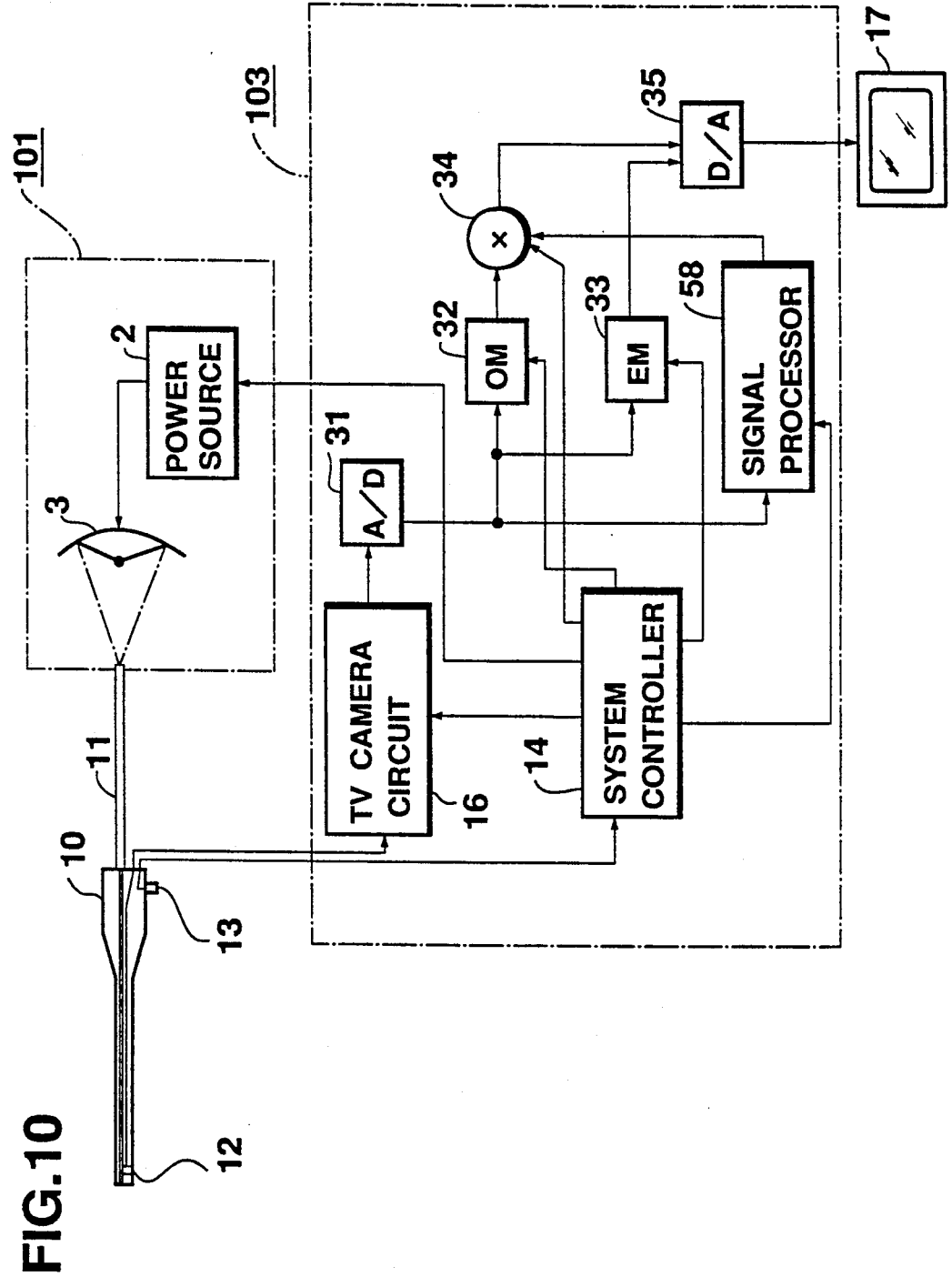
FIG. 10 is a block diagram of a third embodiment of an endoscope according to the present invention.

In FIG. 10, there is shown a third embodiment of an endoscope according to the present invention, having a similar structure to the second embodiment shown in FIG. 7.

In this embodiment, the endoscope comprises a scope 10, a light source section 101 and a processing body section 103. The light source section 101 includes a power source 2 and a light source 3, and the processing body section 103 includes a system controller 14, a TV camera circuit 16, an A/D converter 31, OM and EM memories 32 and 33, a signal processor 58, a multiplier 34, a D/A converter 35 and a display 17, as hereinafter described in detail.

Figure 11:
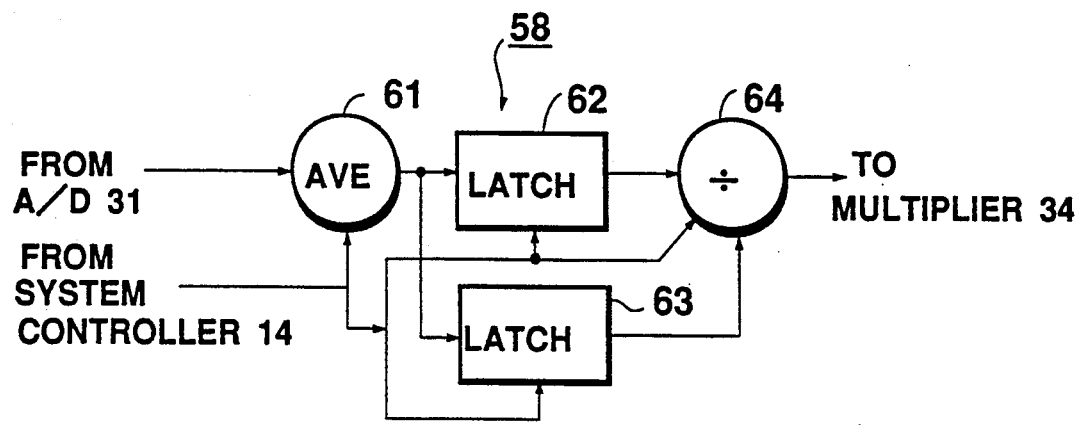
FIG. 11 is a block diagram of a signal processor shown in FIG. 10.

In FIG. 11, there is shown one embodiment of the signal processor 58 for operating a ratio between odd and even field picture image illuminances of a light pulse. The signal processor comprises an average value calculator circuit (AVE) 61, a pair of latch circuits (LATCHs) 62 and 63 and a divider circuit 64, as hereinafter described in detail.

Figure 12:
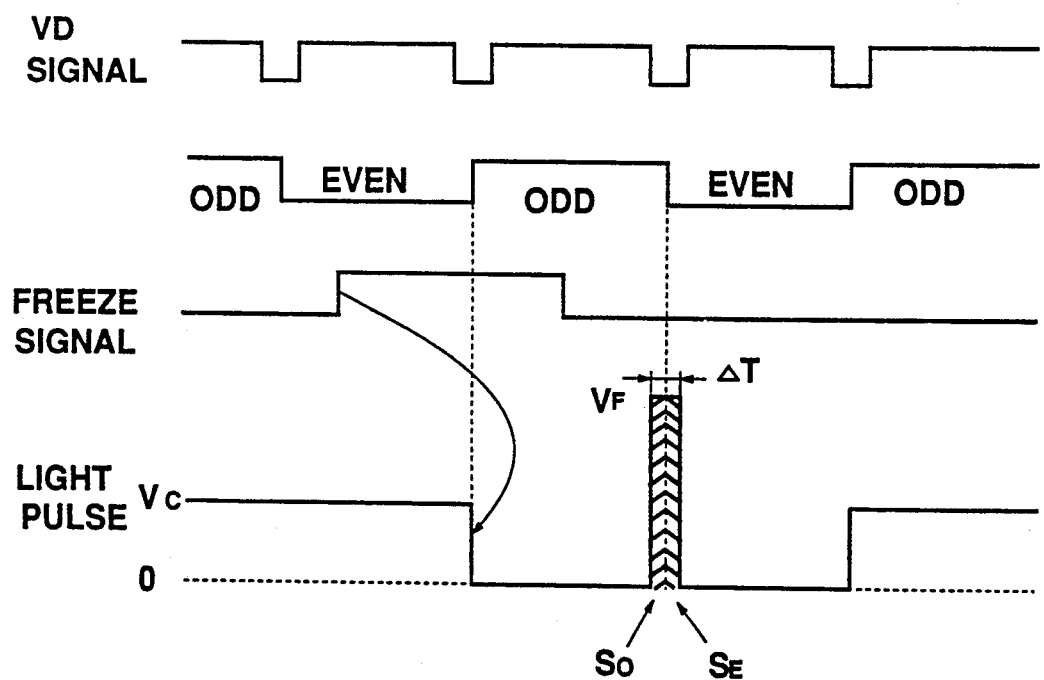
FIG. 12 is a timing chart, like FIG. 9 schematically showing an operation for obtaining a frame of picture image in the endoscope shown in FIG. 10.

FIG. 12 shows a VD signal, a freeze signal and a light pulse having illuminance $V_F$ and time length $\Delta T$ such as 1 to 2 milliseconds in the same manner as those shown in FIG. 9.

When the freeze switch 13 is switched on, a strong light pulse is emitted from the light source 3 for a quite short period $\Delta T$, extending over the boundary between the adjacent odd and even fields, and the odd and even filed picture image data is stored in the OM and EM memories 32 and 33, respectively, in the same manner as the second embodiment described above.

In this embodiment, the signal processor 58 operates the ratio between the odd and even field picture image illuminances of the light pulse, and then the illuminance ratio is corrected to one when the illuminance ratio is shifted from one, as follows. In the signal processor 58, the frozen odd field picture image data, output from the A/D converter 31, for several picture elements are sent to the AVE 61 and is averaged therein to obtain an average value. The average value is stored in the LATCH 62. Another average value for the even picture image data is obtained in the AVE 61 and is then stored in the LATCH 63 in the same manner as the odd average value described above.

For example, when the odd field illuminance is 1.1 times larger than that of the even field illuminance, the divider circuit 64 outputs a value 1.1 to the multiplier 34. In the multiplier 34, a reciprocal number, e.g., 1/1.1 in this case, of the output of the divider circuit 64 is multiplied as a correction value to the odd field picture image data fed from the OM memory 32 in order to correct the difference between the odd and even field illuminances or to correct the discord or disagreement of the odd and even picture images in the same manner as the second embodiment described above. The operation is carried out and the frozen picture image is displayed on the display 17 in the same manner as the second embodiment. In this embodiment, the same effects and advantages as those obtained in the second embodiment can be resulted.

Although the ratio between the odd and even field picture image illuminances of the light pulse extending over the boundary between the adjacent two odd and even fields can be corrected to one or the difference between the odd and even field picture image illuminances of the light pulse extending over the boundary between the adjacent two odd and even fields can be reduced to zero or at least a certain small value in the preferred embodiments according to the present invention, however, of course, the present invention can be applied to the light pulses which are discontinuous and are located in the adjacent two odd and even fields to be close to each other in the boundary portion between the adjacent two odd and even fields.

Although the present invention is applied to an endoscope having a solid-state image pickup device such as a CCD in the end of a scope, however, of course, the present invention can be applicable to an endoscope including a scope with a fiber scope and an optical camera device in its end portion.

Although the present invention has been described in its preferred embodiments with reference to the accompanying drawings, it is readily understood that the present invention is not restricted to the above described preferred embodiments, and various changes and modifications may be made in the present invention by those skilled in the art without departing from the spirit and scope of the present invention.

What is claimed is:

1. An endoscope including a scope, comprising:
   light source means for emitting at least one light pulse in a boundary portion of adjacent first and second fields;
   means for obtaining photoelectrically a detection signal from the light pulse;
   means for calculating a difference between first and second field illuminances of the light pulse from the detection signal; and
   means for controlling the light source means depending on the difference, to reduce the difference to at least a predetermined value.

2. An endoscope including a scope, comprising:
   light source means for emitting a light pulse extending over a boundary between adjacent first and second fields;

means for obtaining photoelectrically a detection signal from the light pulse;

means for calculating a difference between first and second field illuminances of the light pulse from the detection signal; and means for controlling the light source means depending on the difference; to reduce the difference to at least a predetermined value.

3. The endoscope of claim 1, wherein the controlling means includes means for changing a light pulse emitting timing of the light source means.

4. The endoscope of claim 1, wherein the controlling means includes means for comparing the difference with a first predetermined value to obtain a comparison result, and means for changing a light pulse emitting timing of the light source means only when the comparison result is more than a second predetermined value.

5. The endoscope of claim 4, wherein the first predetermined value is at most 3%.

6. The endoscope of claim 1, wherein the operating means includes first and second summing devices for summing first and second illuminances, respectively, and a subtracter for obtaining a difference between the first and second illuminances.

7. The endoscope of claim 3, wherein the changing means includes a pulse controller.

8. The endoscope of claim 4, wherein the comparing means includes a divider, and the changing means includes a pulse controller.

9. The endoscope of claim 1, wherein the light pulse has time length of approximately 1 to 2 milliseconds.

10. An endoscope including a scope, comprising:
light source means for emitting at least one light pulse locating in a boundary portion of adjacent first and second fields;

means for obtaining photoelectrically a detection signal from the light pulse;

means for calculating a difference between first and second field illuminances of the light pulse from the detection signal; and means for electrically controlling one of the detected first and second field illuminances to reduce the difference to at least a predetermined value.

11. The endoscope of claim 10, wherein the controlling means includes means for multiplying a correction value to one of the first and second field illuminances.

12. The endoscope of claim 11, wherein the multiplying means multiplies a reciprocal of the difference to the larger one of the first and second field illuminances.

13. The endoscope of claim 10, wherein the operating means includes a summing device for alternately summing first or second field illuminances, first and second latches for storing first and second field illuminances, respectively, and a divider for obtaining a ratio between the first and second field illuminances.

14. The endoscope of claim 10, wherein the operating means includes an average operator for alternately calculating first or second field illuminance, first and second latchs for storing first and second field illuminances, respectively, and a divider for obtaining a ratio between the first and second field illuminances.

15. The endoscope of claim 10, wherein the light pulse has a duration of approximately 1 to 2 milliseconds.

* * * * *